US010532989B2

(12) United States Patent
Matusz

(10) Patent No.: US 10,532,989 B2
(45) Date of Patent: Jan. 14, 2020

(54) EPOXIDATION CATALYST, A PROCESS FOR PREPARING THE CATALYST, AND A PROCESS FOR THE PRODUCTION OF AN OLEFIN OXIDE, A 1,2-DIOL, A 1,2-DIOL ETHER, A 1,2-CARBONATE, OR AN ALKANOLAMINE

(75) Inventor: Marek Matusz, Houston, TX (US)

(73) Assignee: SHELL OIL COMPANY, Houston, TX (US)

( * ) Notice: Subject to any disclaimer, the term of this patent is extended or adjusted under 35 U.S.C. 154(b) by 1240 days.

(21) Appl. No.: 12/116,905

(22) Filed: May 7, 2008

(65) Prior Publication Data

US 2008/0281118 A1 Nov. 13, 2008

Related U.S. Application Data

(60) Provisional application No. 60/916,947, filed on May 9, 2007.

(51) Int. Cl.
| | | |
|---|---|---|
| *C07D 301/10* | (2006.01) | |
| *C07C 213/04* | (2006.01) | |
| *B01J 23/68* | (2006.01) | |
| *B01J 27/188* | (2006.01) | |
| *C07C 68/04* | (2006.01) | |
| *B01J 23/00* | (2006.01) | |
| *C07C 29/10* | (2006.01) | |
| *B01J 27/055* | (2006.01) | |

(52) U.S. Cl.
CPC .......... *C07D 301/10* (2013.01); *B01J 23/002* (2013.01); *B01J 23/688* (2013.01); *B01J 27/055* (2013.01); *B01J 27/188* (2013.01); *C07C 29/106* (2013.01); *C07C 68/04* (2013.01); *C07C 213/04* (2013.01); *B01J 2523/00* (2013.01); *Y02P 20/142* (2015.11)

(58) Field of Classification Search
CPC .................................................... C07D 301/10
See application file for complete search history.

(56) References Cited

U.S. PATENT DOCUMENTS

| | | | | |
|---|---|---|---|---|
| 1,976,677 | A | 10/1934 | Wittwer | 260/106 |
| 2,219,575 | A | 10/1940 | McNamee et al. | |
| 3,893,910 | A | 7/1975 | Robson | |
| 3,950,507 | A | 4/1976 | Boreskov et al. | |
| 3,962,136 | A | 6/1976 | Nielsen et al. | |
| 4,007,135 | A | 2/1977 | Hayden et al. | |
| 4,010,115 | A | 3/1977 | Nielsen et al. | |
| 4,012,425 | A | 3/1977 | Nielsen et al. | |
| 4,039,561 | A | 8/1977 | Mitsuhata et al. | |
| 4,097,414 | A | 6/1978 | Cavitt | |
| 4,102,820 | A | 7/1978 | Cavitt | |
| 4,206,128 | A | 6/1980 | Cavitt | |
| 4,212,772 | A | 7/1980 | Koopmann et al. | |
| 4,224,194 | A | 9/1980 | Cavitt | |
| 4,226,782 | A | 10/1980 | Hayden et al. | |
| 4,242,235 | A | 12/1980 | Cognion et al. | |
| 4,321,206 | A | 3/1982 | Cavitt | |
| 4,356,312 | A | 10/1982 | Nielsen et al. | |
| 4,379,134 | A | 4/1983 | Weber et al. | |
| 4,389,338 | A | 6/1983 | Mitsuhata et al. | |
| 4,400,559 | A | 8/1983 | Bhise | |
| 4,410,453 | A | 10/1983 | Kiovsky et al. | |
| 4,419,222 | A | 12/1983 | Grenoble et al. | |
| 4,428,863 | A | 1/1984 | Fry | |
| 4,430,312 | A | 2/1984 | Eickmeyer | 423/223 |
| 4,465,754 | A | 8/1984 | Kuin et al. | |
| 4,508,927 | A | 4/1985 | Bhise et al. | |
| 4,555,501 | A | 11/1985 | Armstrong | |
| 4,701,187 | A | 10/1987 | Choe et al. | |
| 4,761,394 | A | 8/1988 | Lauritzen | 502/348 |
| 4,766,105 | A * | 8/1988 | Lauritzen | 502/216 |
| 4,808,738 | A | 2/1989 | Lauritzen | 549/536 |
| 4,820,675 | A | 4/1989 | Lauritzen | 502/216 |
| 4,822,900 | A | 4/1989 | Hayden | 549/534 |
| 4,831,162 | A | 5/1989 | Nakajima et al. | 549/534 |

(Continued)

FOREIGN PATENT DOCUMENTS

| | | | |
|---|---|---|---|
| CA | 1002575 | 1/1985 | ............. B01D 53/34 |
| CA | 2491523 A1 | 1/2004 | |

(Continued)

OTHER PUBLICATIONS

Brunauer, Emmet & Teller, J. Am. Chem. Soc. 60 (1938); pp. 309-316.
J. M. Kobe et al, Ency. Of Catalysis, vol. 3, I'T. Korrath (Ed.), p. 246, published Dec. 2002.
Intercom Article, p. 22, Apr. 2002, Workshop on Safety at SNR—Forum: 100 Years Shell Pernis (English translation provided).
"Kirk-Othmer Encyclopedia of Chemical Technology", 3rd edition, vol. 9, 1980, pp. 445-447.
Starkweather, H.W.: Polymerization Under High Pressure, Beilstein Institute for Organic Chemistry, J. Frankfurt-Main,Am., Chem. Society, vol. 56, pp. 1870-1872.

(Continued)

*Primary Examiner* — Joseph R Kosack

(57) ABSTRACT

A catalyst for the epoxidation of an olefin comprising a carrier and, deposited on the carrier, silver, a rhenium promoter, a first co-promoter, and a second co-promoter; wherein the quantity of the rhenium promoter deposited on the carrier is greater than 1 mmole/kg, relative to the weight of the catalyst;
the first co-promoter is selected from sulfur, phosphorus, boron, and mixtures thereof; the second co-promoter is selected from tungsten, molybdenum, chromium, and mixtures thereof; and
the total quantity of the first co-promoter and the second co-promoter deposited on the carrier is at most 3.8 mmole/kg, relative to the weight of the catalyst;
a process for preparing the catalyst; a process for preparing an olefin oxide by reacting a feed comprising an olefin and oxygen in the presence of the catalyst; and a process for preparing a 1,2-diol, a 1,2-diol ether, a 1,2-carbonate, or an alkanolamine.

17 Claims, 1 Drawing Sheet

(56) References Cited

U.S. PATENT DOCUMENTS

| | | | |
|---|---|---|---|
| 4,845,296 A | 7/1989 | Ahmed et al. | 564/477 |
| 4,874,879 A | 10/1989 | Lauritzen et al. | 549/536 |
| 4,908,343 A | 3/1990 | Bhasin | 502/218 |
| 4,916,243 A | 4/1990 | Bhasin et al. | |
| 4,939,114 A | 7/1990 | Nojiri et al. | |
| 4,994,588 A | 2/1991 | Kapicak et al. | |
| 5,012,027 A | 4/1991 | Abrevaya et al. | |
| 5,051,395 A | 9/1991 | Mitchell et al. | |
| 5,057,481 A | 10/1991 | Bhasin | |
| 5,063,195 A | 11/1991 | Jin et al. | |
| 5,100,859 A | 3/1992 | Gerdes et al. | |
| 5,102,848 A | 4/1992 | Soo et al. | 502/218 |
| 5,106,802 A | 4/1992 | Horiuchi et al. | |
| 5,112,795 A | 5/1992 | Minahan et al. | 502/324 |
| 5,145,658 A | 9/1992 | Chao | 423/232 |
| 5,155,242 A | 10/1992 | Shankar et al. | |
| 5,187,140 A | 2/1993 | Thorsteinson et al. | 502/348 |
| 5,374,738 A | 12/1994 | Boen et al. | |
| 5,380,697 A | 1/1995 | Matusz et al. | 502/348 |
| 5,380,885 A | 1/1995 | Kemp | 549/536 |
| 5,395,812 A | 3/1995 | Nagase et al. | 502/238 |
| 5,407,888 A | 4/1995 | Herzog et al. | |
| 5,418,202 A | 5/1995 | Evans et al. | |
| 5,428,202 A | 6/1995 | Rossi | 219/110 |
| 5,444,034 A | 8/1995 | Rizkalla | |
| 5,486,628 A | 1/1996 | Kemp | |
| 5,504,052 A | 4/1996 | Rizkalla et al. | |
| 5,504,053 A | 4/1996 | Chou et al. | 502/348 |
| 5,597,773 A | 1/1997 | Evans et al. | 502/348 |
| 5,646,087 A | 7/1997 | Rizkalla et al. | 502/347 |
| 5,703,253 A | 12/1997 | Evans et al. | 549/536 |
| 5,705,661 A | 1/1998 | Iwakura et al. | 549/536 |
| 5,736,483 A | 4/1998 | Rizkalla | |
| 5,739,075 A | 4/1998 | Matusz | 502/302 |
| 5,770,746 A | 6/1998 | Cooker et al. | |
| 5,780,656 A | 7/1998 | Rizkalla et al. | |
| 5,801,259 A | 9/1998 | Kowaleski | 549/536 |
| 5,840,932 A | 11/1998 | Evans et al. | 549/512 |
| 5,852,219 A | 12/1998 | Sauer et al. | |
| 5,854,167 A | 12/1998 | Rizkalla et al. | |
| 5,856,534 A | 1/1999 | Cooker et al. | |
| 5,929,259 A | 7/1999 | Lockemeyer | |
| 5,965,481 A | 10/1999 | Durand et al. | |
| 6,040,467 A | 3/2000 | Papavassiliou et al. | 549/534 |
| 6,080,897 A | 6/2000 | Kawabe | 568/858 |
| 6,087,299 A | 7/2000 | Grub et al. | |
| 6,251,820 B1 | 6/2001 | Tsuji | |
| 6,254,666 B1 | 7/2001 | Li et al. | |
| 6,368,998 B1 | 4/2002 | Lockemeyer | 502/347 |
| 6,372,925 B1 | 4/2002 | Evans et al. | 549/536 |
| 6,452,027 B1 | 9/2002 | Billig et al. | 549/538 |
| 6,498,122 B2 | 12/2002 | Nakashiro | |
| 6,498,259 B1 | 12/2002 | Grey et al. | |
| 6,504,053 B1 | 1/2003 | Chaturvedi et al. | |
| 6,511,938 B1 | 1/2003 | Liu et al. | 502/347 |
| 6,533,843 B2 | 3/2003 | Billig et al. | 95/172 |
| 6,534,441 B1 | 3/2003 | Bartley et al. | |
| 6,579,825 B2 | 6/2003 | Lockemeyer | |
| 6,600,056 B1 | 7/2003 | Mikawa et al. | |
| 6,656,874 B2 | 12/2003 | Lockemeyer | |
| 6,750,173 B2 | 6/2004 | Rizkalla et al. | |
| 6,762,311 B2 | 7/2004 | Rizkalla et al. | |
| 6,908,879 B1 | 6/2005 | Shima et al. | |
| 7,102,022 B2 | 9/2006 | Evans et al. | |
| 8,921,586 B2 | 12/2014 | Matusz | |
| 8,932,979 B2 | 1/2015 | Matusz et al. | |
| 8,999,882 B2 | 4/2015 | Lockemeyer et al. | |
| 2002/0010094 A1 | 1/2002 | Lockemeyer | |
| 2003/0162984 A1 | 8/2003 | Lockemeyer et al. | |
| 2003/0191019 A1 | 10/2003 | Rizkalla et al. | |
| 2004/0049061 A1 | 3/2004 | Lockemeyer et al. | 549/536 |
| 2004/0110971 A1 | 6/2004 | Evans et al. | |
| 2004/0110973 A1 | 6/2004 | Matusz | |
| 2004/0198992 A1 | 10/2004 | Matusz et al. | |
| 2005/0222442 A1 | 10/2005 | Lockemeyer | 549/534 |
| 2007/0185339 A1 | 8/2007 | Lu | |
| 2007/0225511 A1 | 9/2007 | Bortinger et al. | |

FOREIGN PATENT DOCUMENTS

| | | | |
|---|---|---|---|
| CA | 2525521 A1 | 11/2004 | |
| CN | 1665796 | 9/2005 | |
| EP | 3642 | 8/1979 | C07D 301/10 |
| EP | 226234 | 8/1980 | |
| EP | 176253 | 9/1984 | |
| EP | 00266015 | 3/1985 | |
| EP | 161930 | 11/1985 | |
| EP | 176253 | 4/1986 | C07D 301/10 |
| EP | 211521 | 2/1987 | |
| EP | 266852 | 11/1987 | |
| EP | 266015 | 4/1988 | |
| EP | 352849 | 7/1989 | |
| EP | 352850 | 7/1989 | |
| EP | 326392 | 8/1989 | |
| EP | 327356 | 8/1989 | |
| EP | 393785 | 10/1990 | C07D 301/10 |
| EP | 425020 | 5/1991 | C07D 301/10 |
| EP | 0425020 | 5/1991 | |
| EP | 448157 | 9/1991 | |
| EP | 480537 | 4/1992 | |
| EP | 0480539 | 4/1992 | |
| EP | 480539 | 4/1992 | C07D 301/10 |
| EP | 496470 | 7/1992 | |
| EP | 0557833 | 9/1993 | |
| EP | 557833 | 9/1993 | C07D 301/10 |
| EP | 567273 | 10/1993 | |
| EP | 0393785 | 1/1995 | |
| EP | 716884 | 6/1996 | B01J 23/66 |
| EP | 933130 | 8/1999 | |
| EP | 1002575 | 5/2000 | B01J 23/04 |
| EP | 0989976 | 4/2002 | |
| EP | 1532125 A1 | 5/2005 | |
| GB | 117663 A | 7/1918 | |
| GB | 119183 A | 9/1918 | |
| GB | 1489335 A | 10/1977 | |
| GB | 1594362 A | 7/1981 | |
| GB | 2161480 | 1/1986 | C07D 301/10 |
| JP | 2006506642 | 2/2006 | |
| JP | 2006522138 | 9/2006 | |
| JP | 2007277744 | 10/2007 | |
| RU | 2045335 | 10/1995 | B01J 23/66 |
| WO | 1995005896 | 3/1995 | |
| WO | 1995007139 | 3/1995 | |
| WO | 1995007754 | 3/1995 | |
| WO | 1995017957 | 7/1995 | |
| WO | 1996004989 | 2/1996 | |
| WO | 1996023585 | 8/1996 | |
| WO | 1996023586 | 8/1996 | |
| WO | 1997040933 | 11/1997 | |
| WO | 1997046317 | 12/1997 | |
| WO | 1998045280 | 10/1998 | |
| WO | 1998058920 | 12/1998 | |
| WO | 1999052883 | 10/1999 | |
| WO | 2000015332 | 3/2000 | |
| WO | 2000015333 | 3/2000 | |
| WO | 2000015334 | 3/2000 | |
| WO | 2000015335 | 3/2000 | |
| WO | 2001096324 | 12/2001 | |
| WO | WO2001096324 | 12/2001 | |
| WO | WO2003072246 | 9/2003 | B01J 23/66 |
| WO | 2004002917 A1 | 1/2004 | |
| WO | WO2004002954 | 1/2004 | |
| WO | WO2004002971 | 1/2004 | C07D 301/10 |
| WO | WO2004002972 | 1/2004 | C07D 301/10 |
| WO | 2004067987 | 8/2004 | |
| WO | 2004078711 A2 | 9/2004 | |
| WO | 2004078736 A1 | 9/2004 | |
| WO | 2004078737 | 9/2004 | |
| WO | WO2004078737 | 9/2004 | C07D 301/10 |
| WO | 2004089537 | 10/2004 | |
| WO | 2004089539 | 10/2004 | |
| WO | 2004092148 A2 | 10/2004 | |
| WO | WO2004089539 | 10/2004 | B01J 23/68 |

(56) References Cited

FOREIGN PATENT DOCUMENTS

| WO | 2004101141 A1 | 11/2004 | |
|---|---|---|---|
| WO | 2005035513 A1 | 4/2005 | |
| WO | 2005097318 A1 | 10/2005 | |
| WO | 2006009756 | 1/2006 | |
| WO | 2006020718 A2 | 2/2006 | |
| WO | WO2006028940 | 3/2006 | ............. B01J 21/04 |
| WO | 2006102189 | 9/2006 | |
| WO | WO2006102189 | 9/2006 | ............... B01J 8/06 |
| WO | 2007092022 A1 | 8/2007 | |
| WO | WO2007122090 | 11/2007 | |
| WO | 2008095453 | 4/2008 | |
| WO | 2009147431 A1 | 12/2009 | |
| WO | 2013072246 | 5/2013 | |

OTHER PUBLICATIONS

Perry, R. H. et al., "Solids Drying and Gas-Solid Systems", Perry's Chemical Engineers Handbook, 6th Ed., Chapter 20, pp. 14-51.
PCT International Search Report dated Jul. 16, 2008 for PCT Application No. US2008/062867 filed May 7, 2008.

\* cited by examiner

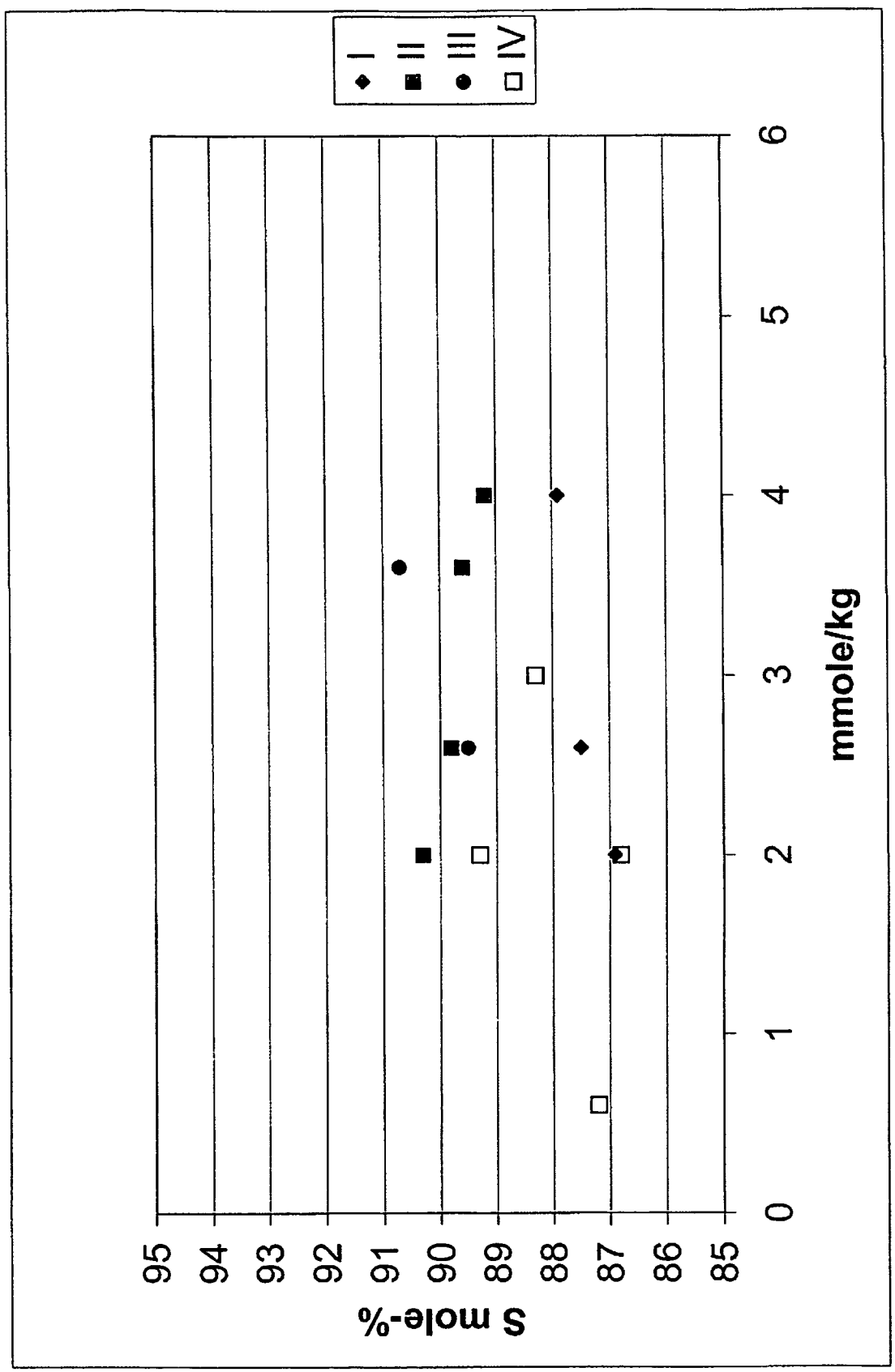

EPOXIDATION CATALYST, A PROCESS FOR PREPARING THE CATALYST, AND A PROCESS FOR THE PRODUCTION OF AN OLEFIN OXIDE, A 1,2-DIOL, A 1,2-DIOL ETHER, A 1,2-CARBONATE, OR AN ALKANOLAMINE

CROSS-REFERENCE TO RELATED APPLICATIONS

This application claims the benefit of U.S. Provisional Patent Application No. 60/916,947, filed May 9, 2007, which is incorporated herein by reference in its entirety.

FIELD OF THE INVENTION

The present invention relates to an epoxidation catalyst, a process for preparing the catalyst, and a process for the production of an olefin oxide, a 1,2-diol, a 1,2-diol ether, a 1,2-carbonate, or an alkanolamine.

BACKGROUND OF THE INVENTION

In olefin epoxidation, a feed containing an olefin and oxygen is contacted with a catalyst under epoxidation conditions. The olefin is reacted with oxygen to form an olefin oxide. A product mix results that contains olefin oxide and, typically, unreacted feed and combustion products.

The olefin oxide may be reacted with water to form a 1,2-diol, with carbon dioxide to form a 1,2-carbonate, with an alcohol to form a 1,2-diol ether, or with an amine to form an alkanolamine. Thus, 1,2-diols, 1,2-carbonates, 1,2-diol ethers, and alkanolamines may be produced in a multi-step process initially comprising olefin epoxidation and then the conversion of the formed olefin oxide with water, carbon dioxide, an alcohol, or an amine.

Olefin epoxidation catalysts typically comprise a silver component, usually with one or more additional elements deposited therewith, on a carrier. U.S. Pat. No. 4,766,105 discloses an ethylene oxide catalyst comprising silver, alkali metal, rhenium and a rhenium co-promoter selected from sulfur, molybdenum, tungsten, chromium and mixtures thereof supported on a carrier. The ethylene oxide catalyst described in U.S. Pat. No. 4,766,105 provides an improvement in one or more catalytic properties.

The catalyst performance may be assessed on the basis of selectivity, activity and stability of operation. The selectivity is the fraction of the converted olefin yielding the desired olefin oxide. As the catalyst ages, the fraction of the olefin converted normally decreases with time and to maintain a constant level of olefin oxide production the temperature of the reaction may be increased.

The selectivity determines to a large extent the economical attractiveness of an epoxidation process. For example, one percent improvement in the selectivity of the epoxidation process can substantially reduce the yearly operating costs of a large scale ethylene oxide plant. Further, the longer the activity and selectivity can be maintained at acceptable values, the longer the catalyst charge can be kept in the reactor and the more product is obtained. Quite modest improvements in the selectivity, activity, and maintenance of the selectivity and activity over long periods yield substantial dividends in terms of process efficiency.

SUMMARY OF THE INVENTION

The present invention provides a catalyst for the epoxidation of an olefin comprising a carrier and, deposited on the carrier, silver, a rhenium promoter, a first co-promoter, and a second co-promoter; wherein the quantity of the rhenium promoter deposited on the carrier is greater than 1 mmole/kg, relative to the weight of the catalyst;

the first co-promoter is selected from sulfur, phosphorus, boron, and mixtures thereof;

the second co-promoter is selected from tungsten, molybdenum, chromium, and mixtures thereof; and the total quantity of the first co-promoter and the second co-promoter deposited on the carrier is at most 3.8 mmole/kg, relative to the weight of the catalyst.

The invention also provides a process for preparing an epoxidation catalyst comprising depositing silver, a rhenium promoter, a first co-promoter, and a second co-promoter on a carrier; wherein the quantity of the rhenium promoter deposited on the carrier is greater than 1 mmole/kg, relative to the weight of the catalyst;

the first co-promoter is selected from sulfur, phosphorus, boron, and mixtures thereof;

the second co-promoter is selected from tungsten, molybdenum, chromium, and mixtures thereof; and the total quantity of the first co-promoter and the second co-promoter deposited on the carrier is at most 3.8 mmole/kg, relative to the weight of the catalyst.

The invention also provides a process for the epoxidation of an olefin comprising reacting the olefin with oxygen in the presence of an epoxidation catalyst prepared according to this invention.

Further, the invention provides a method of preparing a 1,2-diol, a 1,2-diol ether, a 1,2-carbonate, or an alkanolamine comprising obtaining an olefin oxide by the process for the epoxidation of an olefin according to this invention, and converting the olefin oxide into the 1,2-diol, the 1,2-diol ether, the 1,2-carbonate, or the alkanolamine.

BRIEF DESCRIPTION OF THE FIGURE

FIG. 1 shows the selectivity ("S mole-%") as a function of the total quantity of first and second co-promoters ("mmole/kg"), for the various catalysts of Series I, II, III, and IV, described hereinafter.

DETAILED DESCRIPTION OF THE INVENTION

A highly selective epoxidation catalyst comprising a rhenium promoter in a quantity of more than 1 mmole/kg of the catalyst and a catalytically effective amount of silver as well as a first co-promoter and a second co-promoter in a total quantity of at most 3.8 mmole/kg catalyst, in accordance with the invention, exhibits an unexpected improvement in catalytic performance, in particular an improvement in initial selectivity, compared to a like catalyst not in accordance with the invention.

Generally, the epoxidation catalyst is a supported catalyst. The carrier may be selected from a wide range of materials. Such carrier materials may be natural or artificial inorganic materials and they include silicon carbide, clays, pumice, zeolites, charcoal, and alkaline earth metal carbonates, such as calcium carbonate. Preferred are refractory carrier materials, such as alumina, magnesia, zirconia, silica, and mixtures thereof. The most preferred carrier material is α-alumina.

The surface area of the carrier may suitably be at least 0.1 $m^2/g$, preferably at least 0.3 $m^2/g$, more preferably at least 0.5 m²/g, and in particular at least 0.6 m²/g, relative to the weight of the carrier; and the surface area may suitably be at most 20 m²/g, preferably at most 10 m²/g, more preferably at most 6 m²/g, and in particular at most 4 m²/g, relative to the weight of the carrier. "Surface area" as used herein is understood to relate to the surface area as determined by the B.E.T. (Brunauer, Emmett and Teller) method as described in Journal of the American Chemical Society 60 (1938) pp. 309-316. High surface area carriers, in particular when they are alpha alumina carriers optionally comprising in addition silica, alkali metal and/or alkaline earth metal components, provide improved performance and stability of operation.

The water absorption of the carrier may suitably be at least 0.2 g/g, preferably at least 0.25 g/g, more preferably at least 0.3 g/g, most preferably at least 0.35 g/g; and the water absorption may suitably be at most 0.85 g/g, preferably at most 0.7 g/g, more preferably at most 0.65 g/g, most preferably at most 0.6 g/g. The water absorption of the carrier may be in the range of from 0.2 to 0.85 g/g, preferably in the range of from 0.25 to 0.7 g/g, more preferably from 0.3 to 0.65 g/g, most preferably from 0.3 to 0.6 g/g. A higher water absorption may be in favor in view of a more efficient deposition of the metal and promoters on the carrier by impregnation. However, at a higher water absorption, the carrier, or the catalyst made therefrom, may have lower crush strength. As used herein, water absorption is deemed to have been measured in accordance with ASTM C20, and water absorption is expressed as the weight of the water that can be absorbed into the pores of the carrier, relative to the weight of the carrier.

The carrier may be washed, to remove soluble residues, before deposition of the catalyst ingredients on the carrier. Additionally, the materials used to form the carrier, including the burnout materials, may be washed to remove soluble residues. Such carriers are described in U.S. Pat. No. 6,368, 998 and WO-A2-2007/095453, which are incorporated herein by reference. On the other hand, unwashed carriers may also be used successfully. Washing of the carrier generally occurs under conditions effective to remove most of the soluble and/or ionizable materials from the carrier.

The washing liquid may be, for example water, aqueous solutions comprising one or more salts, or aqueous organic diluents. Suitable salts for inclusion in an aqueous solution may include, for example ammonium salts. Suitable ammonium salts may include, for example ammonium nitrate, ammonium oxalate, ammonium fluoride, and ammonium carboxylates, such as ammonium acetate, ammonium citrate, ammonium hydrogencitrate, ammonium formate, ammonium lactate, and ammonium tartrate. Suitable salts may also include other types of nitrates such as alkali metal nitrates, for example lithium nitrate, potassium nitrate and cesium nitrate. Suitable quantities of total salt present in the aqueous solution may be at least 0.001% w, in particular at least 0.005% w, more in particular at least 0.01% w and at most 10% w, in particular at most 1% w, for example 0.03% w. Suitable organic diluents which may or may not be included are, for example, one or more of methanol, ethanol, propanol, isopropanol, tetrahydrofuran, ethylene glycol, ethylene glycol dimethyl ether, diethylene glycol dimethyl ether, dimethylformamide, acetone or methyl ethyl ketone.

The preparation of the silver catalyst is known in the art and the known methods are applicable to the preparation of the catalyst which may be used in the practice of this invention. Methods of depositing silver on the carrier include impregnating the carrier or carrier bodies with a silver compound containing cationic silver and/or complexed silver and performing a reduction to form metallic silver particles. For further description of such methods, reference may be made to U.S. Pat. Nos. 5,380,697, 5,739, 075, 4,766,105, and 6,368,998, which are incorporated herein by reference. Suitably, silver dispersions, for example silver sols, may be used to deposit silver on the carrier.

The reduction of cationic silver to metallic silver may be accomplished during a step in which the catalyst is dried, so that the reduction as such does not require a separate process step. This may be the case if the silver containing impregnation solution comprises a reducing agent, for example, an oxalate, a lactate or formaldehyde.

Appreciable catalytic activity is obtained by employing a silver content of the catalyst of at least 10 g/kg, relative to the weight of the catalyst. Preferably, the catalyst comprises silver in a quantity of from 10 to 500 g/kg, more preferably from 50 to 450 g/kg, for example 105 g/kg, or 120 g/kg, or 190 g/kg, or 250 g/kg, or 350 g/kg. As used herein, unless otherwise specified, the weight of the catalyst is deemed to be the total weight of the catalyst including the weight of the carrier and catalytic components, for example silver, rhenium promoter, first and second co-promoters and further elements, if any.

The catalyst for use in this invention additionally comprises a rhenium promoter component deposited on the carrier in a quantity of greater than 1 mmole/kg, relative to the weight of the catalyst. Preferably, the rhenium promoter may be present in a quantity of at least 1.25 mmole/kg, more preferably at least 1.5 mmole/kg, most preferably at least 2 mmole/kg of the catalyst. Preferably, the rhenium promoter may be present in a quantity of at most 500 mmole/kg, more preferably at most 50 mmole/kg, most preferably at most 10 mmole/kg, relative to the weight of the catalyst. Preferably, the rhenium promoter may be present in a quantity in the range of from 1.25 to 50 mmole/kg, more preferably from 1.75 to 25 mmole/kg, most preferably from 2 to 10 mmole/kg, relative to the weight of the catalyst. The form in which the rhenium promoter may be deposited onto the carrier is not material to the invention. For example, the rhenium promoter may suitably be provided as an oxide or as an oxyanion, for example, as a rhenate or perrhenate, in salt or acid form.

The catalyst for use in this invention additionally comprises a first co-promoter component. The first co-promoter may be selected from sulfur, phosphorus, boron, and mixtures thereof. It is particularly preferred that the first co-promoter comprises, as an element, sulfur.

The catalyst for use in this invention additionally comprises a second co-promoter component. The second co-promoter component may be selected from tungsten, molybdenum, chromium, and mixtures thereof. It is particularly preferred that the second co-promoter component comprises, as an element, tungsten and/or molybdenum, in particular tungsten. The form in which first co-promoter and second co-promoter components may be deposited onto the carrier is not material to the invention. For example, the first co-promoter and second co-promoter components may suitably be provided as an oxide or as an oxyanion, for example, as a tungstate, molybdate, or sulfate, in salt or acid form.

The total quantity of the first co-promoter and the second co-promoter deposited on the carrier is at most 3.8 mmole/kg, calculated as the total quantity of the elements (i.e., the total of sulfur, phosphorous, boron, tungsten, molybdenum and/or chromium) relative to the weight of the catalyst. Preferably, the total quantity of the first co-promoter and the second co-promoter may be at most 3.5 mmole/kg, more preferably at most 3 mmole/kg of catalyst. Preferably, the total quantity of the first co-promoter and the second co-promoter may be at least 0.1 mmole/kg, more preferably at least 0.5 mmole/kg, most preferably at least 1 mmole/kg of the catalyst.

In an embodiment, the molar ratio of the first co-promoter to the second co-promoter may be greater than 1. In this embodiment, the molar ratio of the first co-promoter to the second co-promoter may preferably be at least 1.25, more preferably at least 1.5, most preferably at least 2, in particular at least 2.5. The molar ratio of the first co-promoter to the second co-promoter may be at most 20, preferably at most 15, more preferably at most 10.

In an embodiment, the molar ratio of the rhenium promoter to the second co-promoter may be greater than 1. In this embodiment, the molar ratio of the rhenium promoter to the second co-promoter may preferably be at least 1.25, more preferably at least 1.5. The molar ratio of the rhenium promoter to the second co-promoter may be at most 20, preferably at most 15, more preferably at most 10.

The catalyst may preferably also comprise a further element deposited on the carrier. Eligible further elements may be selected from nitrogen, fluorine, alkali metals, alkaline earth metals, titanium, hafnium, zirconium, vanadium, thallium, thorium, tantalum, niobium, gallium, germanium, and mixtures thereof. Preferably, the alkali metals are selected from lithium, sodium, rubidium and cesium. Most preferably, the alkali metal is lithium, sodium and/or cesium. Preferably, the alkaline earth metals are selected from calcium, magnesium and barium. Preferably, the further element may be present in the catalyst in a total quantity of from 0.01 to 500 mmole/kg, more preferably from 0.5 to 100 mmole/kg, the total quantity of the element relative to the weight of the catalyst. The further element may be provided in any form. For example, salts or hydroxides of an alkali metal or an alkaline earth metal are suitable. For example, lithium compounds may be lithium hydroxide or lithium nitrate.

In an embodiment, the catalyst may preferably further comprise a potassium promoter deposited on the carrier. The additional potassium promoter is preferred especially when the carrier utilized in making the catalyst contains low levels of leachable potassium. For example, the additional potassium promoter is especially preferred when the carrier contains nitric acid leachable potassium in a quantity of less than 85 ppmw, relative to the weight of the carrier, suitably at most 80 ppmw, more suitably at most 75 ppmw, most suitably at most 65 ppmw, same basis. The additional potassium promoter is especially preferred when the carrier contains water leachable potassium in a quantity of less than 40 ppmw, relative to the weight of the carrier, suitably at most 35 ppmw, more suitably at most 30 ppmw. In this embodiment, the potassium promoter may be deposited in a quantity of at least 0.5 mmole/kg, preferably at least 1 mmole/kg, more preferably at least 1.5 mmole/kg, most preferably at least 1.75 mmole/kg, calculated as the total quantity of the potassium deposited relative to the weight of the catalyst. The potassium promoter may be deposited in a quantity of at most 20 mmole/kg, preferably at most 15 mmole/kg, more preferably at most 10 mmole/kg, most preferably at most 5 mmole/kg, on the same basis. The potassium promoter may be deposited in a quantity in the range of from 0.5 to 20 mmole/kg, preferably from 1 to 15 mmole/kg, more preferably from 1.5 to 7.5 mmole/kg, most preferably from 1.75 to 5 mmole/kg, on the same basis. A catalyst prepared in accordance with this embodiment can exhibit an improvement in selectivity, activity, and/or stability of the catalyst especially when operated under conditions where the reaction feed contains low levels of carbon dioxide, described hereinafter.

In an embodiment, the catalyst may preferably contain a quantity of potassium such that the amount of water extractable potassium of the catalyst may be at least 1.25 mmole/kg, relative to the weight of the catalyst, suitably at least 1.5 mmole/kg, more suitably at least 1.75 mmole/kg, same basis. Suitably, the catalyst may contain water extractable potassium in a quantity of at most 10 mmole/kg, more suitably at most 7.5 mmole/kg, most suitably at most 5 mmole/kg, same basis. Suitably, the catalyst may contain water extractable potassium in a quantity in the range of from 1.25 to 10 mmole/kg, more suitably from 1.5 to 7.5 mmole/kg, most suitably from 1.75 to 5 mmole/kg, same basis. The source of water extractable potassium may originate from the carrier and/or the catalytic components. The quantity of water extractable potassium in the catalyst is deemed to be the quantity insofar as it can be extracted from the catalyst. The extraction involves extracting a 2-gram sample of the catalyst three times by heating it in 25-gram portions of de-ionized water for 5 minutes at 100° C. and determining in the combined extracts the amount of potassium by using a known method, for example atomic absorption spectroscopy.

As used herein, unless otherwise specified, the quantity of alkali metal present in the catalyst and the quantity of water leachable components present in the carrier are deemed to be the quantity insofar as it can be extracted from the catalyst or carrier with de-ionized water at 100° C. The extraction method involves extracting a 10-gram sample of the catalyst or carrier three times by heating it in 20 ml portions of de-ionized water for 5 minutes at 100° C. and determining in the combined extracts the relevant metals by using a known method, for example atomic absorption spectroscopy.

As used herein, unless otherwise specified, the quantity of alkaline earth metal present in the catalyst and the quantity of acid leachable components present in the carrier are deemed to be the quantity insofar as it can be extracted from the catalyst or carrier with 10% w nitric acid in de-ionized water at 100° C. The extraction method involves extracting a 10-gram sample of the catalyst or carrier by boiling it with a 100 ml portion of 10% w nitric acid for 30 minutes (1 atm., i.e. 101.3 kPa) and determining in the combined extracts the relevant metals by using a known method, for example atomic absorption spectroscopy. Reference is made to U.S. Pat. No. 5,801,259, which is incorporated herein by reference.

Although the present epoxidation process may be carried out in many ways, it is preferred to carry it out as a gas phase process, i.e. a process in which the feed is contacted in the gas phase with the catalyst which is present as a solid material, typically in a packed bed. Generally the process is carried out as a continuous process.

The olefin for use in the present epoxidation process may be any olefin, such as an aromatic olefin, for example styrene, or a di-olefin, whether conjugated or not, for example 1,9-decadiene or 1,3-butadiene. Typically, the olefin is a monoolefin, for example 2-butene or isobutene. Preferably, the olefin is a mono-α-olefin, for example 1-butene or propylene. The most preferred olefin is ethylene. Suitably, mixtures of olefins may be used.

The quantity of olefin present in the feed may be selected within a wide range. Typically, the quantity of olefin present in the feed will be at most 80 mole-%, relative to the total feed. Preferably, it will be in the range of from 0.5 to 70 mole-%, in particular from 1 to 60 mole-%, on the same basis. As used herein, the feed is considered to be the composition which is contacted with the catalyst.

The present epoxidation process may be air-based or oxygen-based, see "Kirk-Othmer Encyclopedia of Chemical Technology", 3$^{rd}$ edition, Volume 9, 1980, pp. 445-447. In the air-based process, air or air enriched with oxygen is employed as the source of the oxidizing agent while in the oxygen-based processes high-purity (at least 95 mole-%) or very high purity (at least 99.5 mole-%) oxygen is employed as the source of the oxidizing agent. Reference may be made to U.S. Pat. No. 6,040,467, incorporated by reference, for further description of oxygen-based processes. Presently most epoxidation plants are oxygen-based and this is a preferred embodiment of the present invention.

The quantity of oxygen present in the feed may be selected within a wide range. However, in practice, oxygen is generally applied in a quantity which avoids the flammable regime. Typically, the quantity of oxygen applied will be within the range of from 1 to 15 mole-%, more typically from 2 to 12 mole-% of the total feed.

In order to remain outside the flammable regime, the quantity of oxygen present in the feed may be lowered as the quantity of the olefin is increased. The actual safe operating ranges depend, along with the feed composition, also on the reaction conditions such as the reaction temperature and the pressure.

A reaction modifier may be present in the feed for increasing the selectively, suppressing the undesirable oxidation of olefin or olefin oxide to carbon dioxide and water, relative to the desired formation of olefin oxide. Many organic compounds, especially organic halides and organic nitrogen compounds, may be employed as the reaction modifiers. Nitrogen oxides, organic nitro compounds such as nitromethane, nitroethane, and nitropropane, hydrazine, hydroxylamine or ammonia may be employed as well. It is frequently considered that under the operating conditions of olefin epoxidation the nitrogen-containing reaction modifiers are precursors of nitrates or nitrites, i.e. they are so-called nitrate- or nitrite-forming compounds. Reference may be made to EP-A-3642 and U.S. Pat. No. 4,822,900, which are incorporated herein by reference, for further description of nitrogen-containing reaction modifiers.

Organic halides are the preferred reaction modifiers, in particular organic bromides, and more in particular organic chlorides. Preferred organic halides are chlorohydrocarbons or bromohydrocarbons. More preferably they are selected from the group of methyl chloride, ethyl chloride, ethylene dichloride, ethylene dibromide, vinyl chloride or a mixture thereof. Most preferred reaction modifiers are ethyl chloride, vinyl chloride and ethylene dichloride.

Suitable nitrogen oxides are of the general formula $NO_x$ wherein x is in the range of from 1 to 2, and include for example NO, $N_2O_3$ and $N_2O_4$. Suitable organic nitrogen compounds are nitro compounds, nitroso compounds, amines, nitrates and nitrites, for example nitromethane, 1-nitropropane or 2-nitropropane. In preferred embodiments, nitrate- or nitrite-forming compounds, e.g. nitrogen oxides and/or organic nitrogen compounds, are used together with an organic halide, in particular an organic chloride.

The reaction modifiers are generally effective when used in small quantities in the feed, for example up to 0.1 mole-%, relative to the total feed, for example from $0.01 \times 10^{-4}$ to 0.01 mole-%. In particular when the olefin is ethylene, it is preferred that the reaction modifier is present in the feed in a quantity of from $0.1 \times 10^{-4}$ to $500 \times 10^{-4}$ mole-%, in particular from $0.2 \times 10^{-4}$ to $200 \times 10^{-4}$ mole-%, relative to the total feed.

In addition to the olefin, oxygen and the reaction modifier, the feed may contain one or more optional components, such as carbon dioxide, inert gases and saturated hydrocarbons. Carbon dioxide is a by-product in the epoxidation process. However, carbon dioxide generally has an adverse effect on the catalyst activity. Typically, a quantity of carbon dioxide in the feed in excess of 25 mole-%, preferably in excess of 10 mole-%, relative to the total feed, is avoided. A quantity of carbon dioxide of less than 3 mole-%, preferably less than 2 mole-%, in particular in the range of from 0.3 to less than 1 mole-%, relative to the total feed, may be employed. Under commercial operations, a quantity of carbon dioxide of at least 0.1 mole-%, or at least 0.2 mole-%, relative to the total feed, may be present in the feed. Inert gases, for example nitrogen or argon, may be present in the feed in a quantity of from 30 to 90 mole-%, typically from 40 to 80 mole-%. Suitable saturated hydrocarbons are methane and ethane. If saturated hydrocarbons are present, they may be present in a quantity of up to 80 mole-%, relative to the total feed, in particular up to 75 mole-%. Frequently, they are present in a quantity of at least 30 mole-%, more frequently at least 40 mole-%. Saturated hydrocarbons may be added to the feed in order to increase the oxygen flammability limit.

The epoxidation process may be carried out using reaction temperatures selected from a wide range. Preferably the reaction temperature is in the range of from 150 to 325° C., more preferably in the range of from 180 to 300° C.

The epoxidation process is preferably carried out at a reactor inlet pressure in the range of from 1000 to 3500 kPa. "GHSV" or Gas Hourly Space Velocity is the unit volume of gas at normal temperature and pressure (0° C., 1 atm, i.e. 101.3 kPa) passing over one unit volume of packed catalyst per hour. Preferably, when the epoxidation process is a gas phase process involving a packed catalyst bed, the GHSV is in the range of from 1500 to 10000 Nl/(l.h). Preferably, the process is carried out at a work rate in the range of from 0.5 to 10 kmole olefin oxide produced per $m^3$ of catalyst per hour, in particular 0.7 to 8 kmole olefin oxide produced per $m^3$ of catalyst per hour, for example 5 kmole olefin oxide produced per $m^3$ of catalyst per hour. As used herein, the work rate is the amount of the olefin oxide produced per unit volume of catalyst per hour and the selectivity is the molar quantity of the olefin oxide formed relative to the molar quantity of the olefin converted. Suitably, the process is conducted under conditions where the olefin oxide partial pressure in the product mix is in the range of from 5 to 200 kPa, for example 11 kPa, 27 kPa, 56 kPa, 77 kPa, 136 kPa, and 160 kPa. The term "product mix" as used herein is understood to refer to the product recovered from the outlet of an epoxidation reactor.

The olefin oxide produced may be recovered from the product mix by using methods known in the art, for example by absorbing the olefin oxide from a reactor outlet stream in water and optionally recovering the olefin oxide from the aqueous solution by distillation. At least a portion of the aqueous solution containing the olefin oxide may be applied in a subsequent process for converting the olefin oxide into a 1,2-diol, a 1,2-diol ether, a 1,2-carbonate, or an alkanolamine.

The olefin oxide produced in the epoxidation process may be converted into a 1,2-diol, a 1,2-diol ether, a 1,2-carbonate, or an alkanolamine. As this invention leads to a more attractive process for the production of the olefin oxide, it concurrently leads to a more attractive process which comprises producing the olefin oxide in accordance with the invention and the subsequent use of the obtained olefin oxide in the manufacture of the 1,2-diol, 1,2-diol ether, 1,2-carbonate, and/or alkanolamine.

The conversion into the 1,2-diol or the 1,2-diol ether may comprise, for example, reacting the olefin oxide with water, suitably using an acidic or a basic catalyst. For example, for making predominantly the 1,2-diol and less 1,2-diol ether, the olefin oxide may be reacted with a ten fold molar excess of water, in a liquid phase reaction in presence of an acid catalyst, e.g. 0.5-1.0% w sulfuric acid, based on the total reaction mixture, at 50-70° C. at 1 bar absolute, or in a gas phase reaction at 130-240° C. and 20-40 bar absolute, preferably in the absence of a catalyst. The presence of such a large quantity of water may favor the selective formation of 1,2-diol and may function as a sink for the reaction exotherm, helping control the reaction temperature. If the proportion of water is lowered, the proportion of 1,2-diol ethers in the reaction mixture is increased. The 1,2-diol ethers thus produced may be a di-ether, tri-ether, tetra-ether or a subsequent ether. Alternative 1,2-diol ethers may be prepared by converting the olefin oxide with an alcohol, in particular a primary alcohol, such as methanol or ethanol, by replacing at least a portion of the water by the alcohol.

The olefin oxide may be converted into the corresponding 1,2-carbonate by reacting the olefin oxide with carbon dioxide. If desired, a 1,2-diol may be prepared by subsequently reacting the 1,2-carbonate with water or an alcohol to form the 1,2-diol. For applicable methods, reference is made to U.S. Pat. No. 6,080,897, which is incorporated herein by reference.

The conversion into the alkanolamine may comprise, for example, reacting the olefin oxide with ammonia. Anhydrous ammonia is typically used to favor the production of monoalkanolamine. For methods applicable in the conversion of the olefin oxide into the alkanolamine, reference may be made to, for example U.S. Pat. No. 4,845,296, which is incorporated herein by reference.

The 1,2-diol and the 1,2-diol ether may be used in a large variety of industrial applications, for example in the fields of food, beverages, tobacco, cosmetics, thermoplastic polymers, curable resin systems, detergents, heat transfer systems, etc. The 1,2-carbonates may be used as a diluent, in particular as a solvent. Alkanolamines may be used, for example, in the treating ("sweetening") of natural gas.

Unless specified otherwise, the low-molecular weight organic compounds mentioned herein, for example the olefins, 1,2-diols, 1,2-diol ethers, 1,2-carbonates, alkanolamines, and reaction modifiers, have typically at most 40 carbon atoms, more typically at most 20 carbon atoms, in particular at most 10 carbon atoms, more in particular at most 6 carbon atoms. As defined herein, ranges for numbers of carbon atoms (i.e. carbon number) include the numbers specified for the limits of the ranges.

Having generally described the invention, a further understanding may be obtained by reference to the following examples, which are provided for purposes of illustration only and are not intended to be limiting unless otherwise specified.

EXAMPLES

Example 1

Preparation of Stock Silver Solution

This example describes the preparation of a stock silver impregnation solution used in preparing Catalyst A in Example 2.

A silver-amine-oxalate stock solution was prepared by the following procedure:

In a 5-liter stainless steel beaker, 415 g of reagent-grade sodium hydroxide were dissolved in 2340 ml de-ionized water, and the temperature was adjusted to 50° C.

In a 4-liter stainless steel beaker, 1699 g high purity "Spectropure" silver nitrate was dissolved in 2100 ml de-ionized water, and the temperature was adjusted to 50° C.

The sodium hydroxide solution was added slowly to the silver nitrate solution, with stirring, while maintaining a solution temperature of 50° C. This mixture was stirred for 15 minutes. The pH of the solution was maintained at above 10 by the addition of sodium hydroxide solution as required.

Water was removed from the precipitate created in the mixing step and the conductivity of the water, which contained sodium and nitrate ions, was measured. An amount of fresh deionized water equal to the amount removed was added back to the silver solution. The solution was stirred for 15 minutes at 40° C. The process was repeated until the conductivity of the water removed was less than 90 µmho/cm. 1500 ml fresh deionized water was then added. 630 g of high-purity oxalic acid dihydrate were added in approximately 100 g increments. The temperature was kept at 40° C. (±5° C.) and the pH of the solution was monitored during the addition of the last 130 grams of oxalic acid dihydrate to ensure that the pH did not drop below 7.8 for an extended period of time.

Water was removed from this mixture to leave a highly concentrated silver-containing slurry. The silver oxalate slurry was cooled to 30° C.

699 g of 92 weight percent ethylenediamine (8% de-ionized water) was added while maintaining a temperature no greater than 30° C. The final solution was used as a stock silver impregnation solution for preparing Catalyst A.

Example 2

Preparation of Catalysts

Catalyst A:

Catalyst A was prepared by the following procedure: To 404 grams of stock silver solution of specific gravity 1.545 g/ml was added 0.3630 g of ammonium perrhenate in 2 g of 1:1 ethylenediamine/water; 0.1012 g of ammonium meta-tungstate dissolved in 2 g of 1:1 ammonia/water; 0.1732 g of lithium sulfate monohydrate dissolved in 2 g of water; and 0.4259 g of lithium hydroxide monohydrate dissolved in water. Additional water was added to adjust the specific gravity of the solution to 1.528 g/ml. 100 g of the resulting solution was mixed with 0.2727 g of 50% w cesium hydroxide solution, producing the final impregnation solution. A vessel containing 30 grams of Carrier A hollow cylinders, see Table I below, was evacuated to 20 mm Hg for 1 minute and the final impregnation solution was added to Carrier A while under vacuum, then the vacuum was released and the carrier allowed to contact the liquid for 3 minutes. The impregnated Carrier A was then centrifuged at 500 rpm for 2 minutes to remove excess liquid. Impregnated Carrier A was placed in a vibrating shaker and dried in air flowing at a rate of 16.2 Nl/h at 250° C. for 7 minutes producing Catalyst A.

The final composition of Catalyst A comprised the following, calculated on the basis of pore volume impregnation: 17.2% w silver; 2 mmole Re/kg; 0.6 mmole W/kg; 2 mmole S/kg; 19 mmole Li/kg; and 5.6 mmole Cs/kg. These values are relative to the weight of the catalyst.

TABLE I

| Carrier A Properties | |
| --- | --- |
| Surface Area (m²/g) | 0.75 |
| Water Absorption (%) | 47.2 |
| Packing Density (kg/m³) | 838 |
| alpha alumina content (%) | 98.4 |
| Nitric Acid Leachables: | |
| Na | 116 |
| K | 87 |
| Ca | 567 |
| Al | 607 |
| Mg | 81 |
| SiO₂ | 1474 |

Catalyst B:

Catalyst B was prepared in a similar manner as Catalyst A. The final composition of Catalyst B comprised the following, calculated on the basis of pore volume impregnation: 17.2% w silver; 2 mmole Re/kg; 0.6 mmole W/kg; 3 mmole S/kg; 21 mmole Li/kg; and 6.4 mmole Cs/kg. These values are relative to the weight of the catalyst.

Catalyst C:

Catalyst C was prepared in a similar manner as Catalyst A. The final composition of Catalyst C comprised the following, calculated on the basis of pore volume impregnation: 17.5% w silver; 2 mmole Re/kg; 1 mmole W/kg; 1 mmole S/kg; 17 mmole Li/kg; and 4.9 mmole Cs/kg. These values are relative to the weight of the catalyst.

Catalyst D:

Catalyst D was prepared in a similar manner as Catalyst A, using 30 grams of Carrier A. To 198.4 grams of stock silver solution of specific gravity 1.551 g/ml was added 0.1833 g of ammonium perrhenate in 2 g of 1:1 ethylenediamine/water; 0.0362 g of ammonium molybdate dissolved in 2 g of 50:50 ammonium hydroxide/water; 0.1312 g of lithium sulfate monohydrate dissolved in 2 g of water; and 0.2151 g of lithium hydroxide monohydrate dissolved in water. Additional water was added to adjust the specific gravity of the solution to 1.528 g/ml. 50 g of the resulting solution was mixed with 0.1591 g of 50% w cesium hydroxide solution, producing the impregnation solution. This final impregnation solution was used to prepare Catalyst D.

The final composition of Catalyst D comprised the following, calculated on the basis of pore volume impregnation: 17.2% w silver; 2 mmole Re/kg; 0.6 mmole Mo/kg; 3 mmole S/kg; 21 mmole Li/kg; and 6.4 mmole Cs/kg. These values are relative to the weight of the catalyst.

Catalyst E:

Catalyst E was prepared in a similar manner as Catalyst D. The final composition of Catalyst E comprised the following, calculated on the basis of pore volume impregnation: 17.2% w silver; 2 mmole Re/kg; 0.6 mmole Mo/kg; 2 mmole S/kg; 19 mmole Li/kg; and 6 mmole Cs/kg. These values are relative to the weight of the catalyst.

Catalyst F (Comparative):

Catalyst F was prepared in a similar manner as Catalyst A. The final composition of Catalyst F comprised the following, calculated on the basis of pore volume impregnation: 17.2% w silver; 2 mmole Re/kg; 2 mmole W/kg; 2 mmole S/kg; 19 mmole Li/kg; and 5.6 mmole Cs/kg. These values are relative to the weight of the catalyst.

Catalyst G (Comparative):

Catalyst G was prepared in a similar manner as Catalyst A. The final composition of Catalyst G comprised the following, calculated on the basis of pore volume impregnation: 17.5% w silver; 1 mmole Re/kg; 1 mmole W/kg; 1 mmole S/kg; 17 mmole Li/kg; and 4.5 mmole Cs/kg. These values are relative to the weight of the catalyst.

Catalyst H (Comparative):

Catalyst H was prepared in a similar manner as Catalyst A. The final composition of Catalyst H comprised the following, calculated on the basis of pore volume impregnation: 17.5% w silver; 1 mmole Re/kg; 2 mmole W/kg; 2 mmole S/kg; 19 mmole Li/kg; and 4.1 mmole Cs/kg. These values are relative to the weight of the catalyst.

Catalyst I (Comparative):

Catalyst I was prepared in a similar manner as Catalyst A. The final composition of Catalyst I comprised the following, calculated on the basis of pore volume impregnation: 17.5% w silver; 1 mmole Re/kg; 0.6 mmole W/kg; 2 mmole S/kg; 19 mmole Li/kg; and 4.5 mmole Cs/kg. These values are relative to the weight of the catalyst.

Catalyst J (Comparative):

Catalyst J was prepared in a similar manner as Catalyst A. The final composition of Catalyst J comprised the following, calculated on the basis of pore volume impregnation: 17.2% w silver; 2 mmole Re/kg; 0.6 mmole W/kg; 15 mmole Li/kg; and 5.6 mmole Cs/kg. These values are relative to the weight of the catalyst.

Catalyst K (Comparative):

Catalyst K was prepared in a similar manner as Catalyst A. The final composition of Catalyst K comprised the following, calculated on the basis of pore volume impregnation: 17.2% w silver; 2 mmole Re/kg; 2 mmole W/kg; 15 mmole Li/kg; and 4.1 mmole Cs/kg. These values are relative to the weight of the catalyst.

Catalyst L (Comparative):

Catalyst L was prepared in a similar manner as Catalyst A. The final composition of Catalyst L comprised the following, calculated on the basis of pore volume impregnation: 17.2% w silver; 2 mmole Re/kg; 3 mmole S/kg; 21 mmole Li/kg; and 6.8 mmole Cs/kg. These values are relative to the weight of the catalyst.

Catalyst M (Comparative):

Catalyst M was prepared in a similar manner as Catalyst A. The final composition of Catalyst M comprised the following, calculated on the basis of pore volume impregnation: 17.2% w silver; 2 mmole Re/kg; 2 mmole S/kg; 19 mmole Li/kg; and 5.6 mmole Cs/kg. These values are relative to the weight of the catalyst.

The cesium amounts of the above catalysts are the optimized cesium amounts with respect to the initial selectivity performance of the catalysts.

Example 3

Testing of Catalysts

The catalysts were used to produce ethylene oxide from ethylene and oxygen. To do this, 3 to 5 g of the crushed catalyst samples were loaded into separate stainless steel U-shaped tubes. Each tube was immersed in a molten metal bath (heat medium) and the ends were connected to a gas flow system. The weight of catalyst used and the inlet gas flow rate were adjusted to give a gas hourly space velocity of 3300 Nl/(l.h), as calculated for uncrushed catalyst. The inlet gas pressure was 1550 kPa (absolute).

The gas mixture passed through the catalyst bed, in a "once-through" operation, during the entire test run, consisted of 30.0 volume percent ethylene, 8.0 volume percent oxygen, 5.0 volume percent carbon dioxide, 57 volume percent nitrogen and 0 to 4.0 parts per million by volume (ppmv) ethyl chloride.

Prior to startup, the catalysts were pre-treated for 3 hours with a gas mixture of 11.4 mole-% oxygen, 7 mole-% carbon dioxide and 81.6 mole-% nitrogen at 280° C., except Catalysts A, B, J, and M which were pre-treated for 3 hours under a flow of nitrogen at 225° C. Then the reactor was either cooled down or heated to 240° C. and testing gas mixture was introduced. The temperature was then adjusted so as to achieve a constant ethylene oxide content of 3.09 volume percent in the outlet gas stream. The quantity of ethyl chloride was varied to obtain maximum selectivity. Catalysts B, E and L were additionally subjected to conditions where the ethyl chloride was decreased to zero for 4 to 24 hours during which time the temperature was changed to 250-260° C. Initial performance data at this conversion level was measured between 1 to 7 days of operation. The performance data is summarized below in Table II. Selectivity and temperature values corresponding to increasing cumulative ethylene oxide production would also be measured in order to obtain catalyst stability data.

As observed from the data in Table II, Catalysts A, B, C, D, and E, having a total quantity of first and second co-promoters of at most 3.8 mmole/kg catalyst, exhibit an unexpected improvement in initial selectivity at the same ethylene oxide production levels, relative to Catalyst F which has a total quantity of first and second co-promoters of 4 mmole/kg catalyst. This technical effect is shown in FIG. 1. FIG. 1 is a graph showing the selectivity (S mole-%) relative to the total quantity of co-promoter(s) (mmole/kg).

Series II relates to Catalysts A, B, C, and F which contain 2 mmole of rhenium per kilogram of catalyst, sulfur as the first co-promoter, and tungsten as the second co-promoter. Series III relates to Catalysts D and E which contain 2 mmole of rhenium per kilogram of catalyst; sulfur as the first co-promoter; molybdenum as the second co-promoter.

Series I relates to Catalysts G, H and I which contain 1 mmole of rhenium per kilogram of catalyst, sulfur as the first co-promoter, and tungsten as the second co-promoter. The advantage in initial selectivity was not observed for the catalysts of Series I.

Series IV relates to Catalysts J, K, L, and M which contain 2 mmole of rhenium per kilogram of catalyst and either a first co-promoter of sulfur or a second co-promoter of tungsten.

Example 4

Catalyst N was prepared using Carrier B and having a final composition of the following, calculated on the basis of pore volume impregnation: 17.5% w silver; 2 mmole Re/kg; 0.6 mmole W/kg; 2 mmole S/kg; 19 mmole Li/kg; 2 mmole K/kg; and 3.8 mmole Cs/kg. These values are relative to the weight of the catalyst. Ammonium perrhenate, ammonium metatungstate, ammonium sulfate, lithium hydroxide, potassium nitrate and cesium hydroxide were used to prepare Catalyst N.

TABLE III

| Carrier B Properties | |
|---|---|
| Surface Area ($m^2/g$) | 0.73 |
| Water Absorption (%) | 47.8 |
| Packing Density ($kg/m^3$) | 838 |
| alpha alumina content (%) | 98.4 |
| Nitric Acid Leachable, ppmw: | |
| Na | 131 |
| K | 83 |
| Ca | 533 |
| Al | 655 |
| Mg | 74 |
| $SiO_2$ | 1456 |

A tubular pilot reactor was charged with 12.24 kg of whole catalyst pellets in the form of a hollow cylinder having a nominal outer diameter of 8 mm, a nominal inner diameter of 1 mm and a nominal length of 8 mm. The coolant (water) surrounding the tubular reactor was heated from 40 to 220° C. over 17 hours and a flow of $N_2$ gas at GHSV of 1100 Nl/l/h was introduced into the reactor tube. Once the coolant temperature reached 220° C., ethylene was added to the reactor feed gas and brought to 25 vol %. After the desired ethylene concentration was achieved, air was introduced in the reactor feed to initiate reaction of ethylene and oxygen to ethylene oxide. At essentially the same time as air was introduced to the reactor, ethyl chloride was introduced and brought to a concentration of 2-2.5 ppmv. During the next 6 hours of operation, the air feed rate was increased until an oxygen concentration of 4.0 vol % was achieved at the reactor inlet. As the oxygen was increased, the coolant temperature was increased to 235° C., carbon dioxide was introduced and brought to 0.8 vol %, and the

TABLE II

| Catalyst | Series | Cs (mmole/kg) | Ag Content % w | Re (mmole/kg) | W (mmole/kg) | Mo (mmole/kg) | S (mmole/kg) | Total Co-Promoters (mmole/kg) | Selectivity Initial (%) | Temperature Initial (° C.) |
|---|---|---|---|---|---|---|---|---|---|---|
| A *) | II | 5.6 | 17.2 | 2 | 0.6 | — | 2 | 2.6 | 89.8 | 250 |
| B *) | II | 6.4 | 17.2 | 2 | 0.6 | — | 3 | 3.6 | 89.6 | 251 |
| C *) | II | 4.9 | 17.5 | 2 | 1 | — | 1 | 2 | 90.3 | 262 |
| D *) | III | 6.4 | 17.2 | 2 | — | 0.6 | 3 | 3.6 | 90.7 | 261 |
| E *) | III | 6.0 | 17.2 | 2 | — | 0.6 | 2 | 2.6 | 89.5 | 261 |
| F **) | II | 5.6 | 17.2 | 2 | 2 | — | 2 | 4 | 89.2 | 268 |
| G **) | I | 4.5 | 17.5 | 1 | 1 | — | 1 | 2 | 86.9 | 265 |
| H **) | I | 4.1 | 17.5 | 1 | 2 | — | 2 | 4 | 87.9 | 264 |
| I **) | I | 4.5 | 17.5 | 1 | 0.6 | — | 2 | 2.6 | 87.5 | 256 |
| J **) | IV | 5.6 | 17.2 | 2 | 0.6 | — | — | 0.6 | 87.2 | 252 |
| K **) | IV | 4.1 | 17.2 | 2 | 2 | — | — | 2 | 89.3 | 261 |
| L **) | IV | 6.8 | 17.2 | 2 | — | — | 3 | 3 | 88.3 | 251 |
| M **) | IV | 5.6 | 17.2 | 2 | — | — | 2 | 2 | 86.8 | 239 |

*) according to the invention
**) comparative total flow was increased to a GHSV of 3320 Nl/l/h. The inlet pressure to the reactor was maintained at 241 psig throughout the experiment. A total of 0.15 grams of ethyl chloride per kilogram of catalyst was introduced. For the next 17 hours, ethyl chloride was reduced to 1.4 ppmv and all other conditions were held constant at GHSV of 3320 Nl/l/h, 235° C. coolant temperature, 241 psig inlet pressure, and ethylene/oxygen/carbon dioxide composition of 25:4:0.8. During the next 7 hours, ethylene was increased from 25 to 35 vol %, oxygen was increased from 4.0 to 7.5 vol %, and ethyl chloride was increased from 1.4 ppmv to 1.91 ppmv. All other gas flows and compositions were held constant. At the end of this step, the coolant temperature was adjusted to 227° C. to achieve an ethylene oxide concentration of 2.7 vol % in the outlet of the reactor. During the following 24 hours, the ethyl chloride concentration was increased to 2.05 ppmv to obtain the optimal catalyst selectivity. At the end of the start-up process (i.e., during step 6), the selectivity was 90.3% at a temperature of 228° C. Details of the changing reactor conditions are set out in Table IV.

TABLE IV

| Step | Temperature, ° C. | GHSV, Nl/l/h | $O_2$, % | $C_2H_4$, % | $CO_2$, % | Ethyl Chloride, ppmv | Time, h |
|---|---|---|---|---|---|---|---|
| 1 | 40 to 220 | 1100 | 0 | 0 | 0 | 0 | 17 |
| 2 | 220 | 1100 | 0 | 25 | 0 | 0 | 1 |
| 3 | 220 to 235 | 1100 to 3320 | 0 to 4 | 25 | 0-0.8 | 2 to 2.5 | 6 |
| 4 | 235 | 3320 | 4 | 25 | 0.8 | 1.4 | 17 |
| 5 | 235 to 227 | 3320 | 4 to 7.5 | 25 to 35 | 0.8 | 1.4 to 1.91 | 7 |
| 6 | 228 | 3320 | 7.5 | 35 | 0.8 | 2.05 | 24 |

During the start-up process and initial epoxidation production, the quantity of ethylene may be maintained at a constant level and different amounts may be utilized, for example the quantity of ethylene may be 25 mole-%, 35 mole-%, or 40 mole-%. The quantity of oxygen may be varied within flammability limits. The length of step 4 may be varied from 1 to 30 hours, shorter periods of time may be preferred for higher production levels.

What is claimed is:

1. A catalyst for the epoxidation of an olefin comprising a carrier and, deposited on the carrier, silver, a rhenium promoter, a first co-promoter, and a second co-promoter; wherein
   the quantity of the rhenium promoter deposited on the carrier is at least 2 mmole/kg, relative to the weight of the catalyst;
   the first co-promoter is selected from the group consisting of sulfur, phosphorus, boron, and mixtures thereof;
   the second co-promoter is selected from the group consisting of tungsten, molybdenum, chromium, and mixtures thereof; and
   the total quantity of the first co-promoter and the second co-promoter deposited on the carrier is at most 3.8 mmole/kg, relative to the weight of the catalyst.

2. The catalyst as claimed in claim 1, wherein the quantity of the rhenium promoter is from 2 to 10 mmole/kg, relative to the weight of the catalyst.

3. The catalyst as claimed in claim 1, wherein the total quantity of the first co-promoter and the second co-promoter is at most 3.5 mmole/kg, relative to the weight of the catalyst.

4. The catalyst as claimed in claim 1, wherein the total quantity of the first co-promoter and the second co-promoter is at least 0.5 mmole/kg, relative to the weight of the catalyst.

5. The catalyst as claimed in claim 1, wherein the second co-promoter comprises tungsten.

6. The catalyst as claimed in claim 1, wherein the second co-promoter comprises molybdenum.

7. The catalyst as claimed in claim 1, wherein the first co-promoter comprises sulfur.

8. The catalyst as claimed in claim 1, wherein the catalyst further comprises a further element selected from the group consisting of nitrogen, fluorine, alkali metals, alkaline earth metals, titanium, hafnium, zirconium, vanadium, thallium, thorium, tantalum, niobium, gallium and germanium and mixtures thereof.

9. The catalyst as claimed in claim 8, wherein the alkali metals are selected from the group consisting of lithium, sodium, and cesium.

10. The catalyst as claimed in claim 1, wherein the catalyst further comprises deposited on the carrier a potassium promoter in a quantity of at least 0.5 mmole/kg, relative to the weight of the catalyst.

11. The catalyst as claimed in claim 1, wherein the catalyst further comprises deposited on the carrier a potassium promoter in a quantity of at least 1.5 mmole/kg, relative to the weight of the catalyst.

12. The catalyst as claimed in claim 1, wherein the catalyst has a water extractable quantity of potassium in the range of from 1.25 to 10 mmole/kg, relative to the weight of the catalyst.

13. The catalyst as claimed in claim 1, wherein the catalyst has a water extractable quantity of potassium in the range of from 1.5 to 7.5 mmole/kg, relative to the weight of the catalyst.

14. The catalyst as claimed in claim 1, wherein silver is present in a quantity in the range of 10 to 500 g/kg, relative to the weight of the catalyst.

15. The catalyst as claimed in claim 1, wherein silver is present in a quantity in the range of 50 to 450 g/kg, relative to the weight of the catalyst.

16. The catalyst as claimed in claim 1, wherein the molar ratio of the first co-promoter to the second co-promoter is greater than 2.

17. The catalyst as claimed in claim 1, wherein the molar ratio of the first co-promoter to the second co-promoter is greater than 2 and at most 20.

* * * * *